United States Patent [19]

Schulte-Elte et al.

[11] Patent Number: 4,487,944
[45] Date of Patent: Dec. 11, 1984

[54] ACETYLENIC AND ALLENIC CARBINOLS, THEIR UTILIZATION AS STARTING MATERIALS FOR THE PREPARATION OF β-DAMASCENONE AND PROCESS FOR PREPARING SAME

[75] Inventors: Karl-Heinrich Schulte-Elte, Onex; Bernard Müller, Geneva, both of Switzerland

[73] Assignee: Firmenich, SA, Switzerland

[21] Appl. No.: 536,258

[22] Filed: Sep. 27, 1983

[30] Foreign Application Priority Data

Nov. 18, 1982 [CH] Switzerland .................. 6713/82

[51] Int. Cl.³ .................. C07D 309/06; C07C 49/543
[52] U.S. Cl. .................. 549/416; 556/436; 556/449; 568/347; 568/378; 568/591; 568/668
[58] Field of Search .................. 568/378; 549/416; 556/436

[56] References Cited

U.S. PATENT DOCUMENTS

| | | | |
|---|---|---|---|
| 3,400,158 | 9/1968 | Roberts | 568/378 |
| 3,576,880 | 4/1971 | Weedon et al. | 568/378 |
| 4,324,729 | 4/1982 | Fankhauser | 568/378 |
| 4,405,417 | 9/1983 | Grass et al. | 568/378 |
| 4,453,013 | 6/1984 | Fankhauser | 549/416 |

Primary Examiner—Nicky Chan

Attorney, Agent, or Firm—Scully, Scott, Murphy & Presser

[57] ABSTRACT

New acetylenic and allenic carbinols of formula

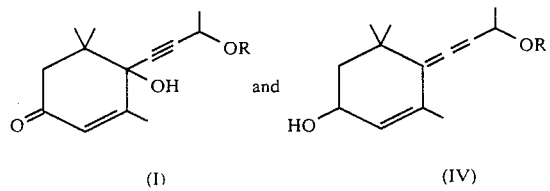

respectively, wherein symbol R stands for a trialkylsilyl or a $C_1$ to $C_6$ alkyl radical, preferably a methyl, a tert-butyl or an isoamyl radical, or a group of formula

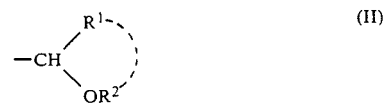

wherein, when taken separately, each of symbols $R^1$ and $R^2$ represents a lower alkyl radical or, when taken together, $R^1$ and $R^2$ represent a tetramethylene group, are useful intermediates for the preparation of β-damascenone.

2 Claims, No Drawings

ACETYLENIC AND ALLENIC CARBINOLS, THEIR UTILIZATION AS STARTING MATERIALS FOR THE PREPARATION OF β-DAMASCENONE AND PROCESS FOR PREPARING SAME

THE INVENTION

The instant invention relates to new acetylenic and allenic carbinols of formula

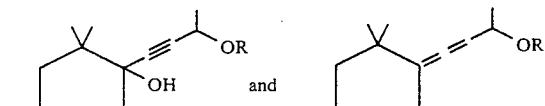

respectively, wherein symbol R stands for a trialkyl-silyl or a $C_1$ to $C_6$ alkyl radical, preferably a methyl, a tert-butyl or an isoamyl radical, or a group of formula

wherein, when taken separately, each of symbols $R^1$ and $R^2$ represents a lower alkyl radical or, when taken together, $R^1$ and $R^2$ represents a tetramethylene group.

The invention provides a process for the preparation of said carbinols (I) which process comprises the steps of reacting 2,2,6-trimethyl-cyclohex-5-en-1,4-dione ("oxophorone") with an organo-metallic derivative of formula

wherein symbol ME represents a magnesium-halide radical and R is defined as indicated above for formula (I), and subsequently hydrolysing the resulting reaction product.

This invention also provides a process for the preparation of carbinols (IV) which process comprises the steps of reacting 2,2,6-trimethyl-cyclohex-5-en-1,4-dione ("oxophorone") with an organo-metallic derivative of formula

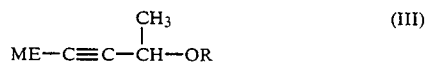

wherein symbol ME represents a magnesium-halide radical and R is defined as indicated above for formula (I), and of reducing the resulting reaction product with a metal hydride in the presence of an inert organic solvent belonging to the class of aromatic hydrocarbons or ethers.

BACKGROUND OF THE INVENTION

β-Damascenone, an alicyclic ketone of formula

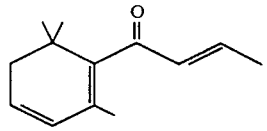

is particularly well appreciated in the art of perfumery and flavors. Its utilization as perfuming and flavoring ingredient is the object of several patents, viz. U.S. Pat. No. 3,975,310, Swiss Pat. Nos. 520,479 and 509,399. Many syntheses have been proposed in the past for preparing β-damascenone, the most interesting ones being cited hereinafter:

dehydrogenation of the corresponding cyclohexenic compound, viz. β-damascone (see Swiss Pat. No. 505,773);

treatment of 1-(2,6,6-trimethyl-1,2-epoxy-cyclohexyl)-but-2-en-1-one with an acidic dehydrating agent (see DE-AS No. 20 65 322), and treatment of 4-(2,6,6-trimethyl-1-hydroxy-cyclohex-2-en-1-yl)-but-3-yn-2-ol with an acidic dehydrating agent (see DE-PS No. 22 42 751).

Despite the existence of several synthetic methods there exists the constant need to improve the yield of the existing methods or to elaborate new and original syntheses, namely syntheses starting from cheaper or more accessible raw materials. The invention provides an efficient solution to this problem.

PREFERRED EMBODIMENTS OF THE INVENTION

The first step of the preparation of the acetylenic carbinols of formula (I) consists in reacting 2,2,6-trimethyl-cyclohex-5-en-1,4-dione with an organo-metallic derivative of formula (III), according to a method usual in the art. Symbol ME in formula (III) represents a magnesium halide radical such as MgBr, MgCl or MgI. The bromo-magnesium derivative is used preferably, in the conditions of a Grignard reaction.

As indicated above, symbol R in formula (III) may either represent a trialkyl-silyl radical, a $C_1$ to $C_6$ alkyl radical, preferably a methyl, a tert-butyl or an isoamyl radical, or a group of formula

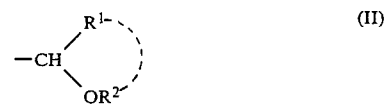

wherein, when taken separately, each of symbols $R^1$ and $R^2$ represents a lower alkyl radical, e.g. methyl, ethyl or propyl. Symbol R can also represent a tetrahydropyranyl radical, i.e. a group wherein in formula (II) both $R^1$ and $R^2$ are taken together and represent a tetramethylene group. In fact, R is deemed to represent any protecting group of the hydroxy function which is stable in a basic medium and easily hydrolisable under acidic conditions.

According to the process of the present invention, the resulting product is then hydrolyzed in the reaction mixture in accordance with the usual technique.

Allenic carbinols (IV) are prepared according to the invention by a process which eminently consists of the addition of organo-metallic derivative of formula (III) to 2,2,6-trimethyl-cyclohex-5-en-1,4-dione, in perfect analogy with the first step of the above described process for the preparation of the compounds of formula (I), followed by the reduction of the resulting reaction product by means of a metal hydride in the presence of an organic solvent, inert under the reaction conditions chosen, selected from the class of aromatic hydrocarbons and ethers.

A preferred metal hydride is diethyl sodium-aluminohydride (OMH). Suitable solvents include benzene, toluene, diethyl ether and tetrahydrofuran.

According to a variant of the above described process, allenic carbinols (IV) can be obtained from acetylenic carbinols (I) via a reduction by means of, for instance, OMH, lithium aluminium hydride of DiBAH (diisobutyl aluminium hydride).

Allenic carbinols of formula (IV) represent useful starting materials for the preparation of β-damascenone. Their conversion into β-damascenone is effected by means of a diluted strong acid of mineral or organic origin. Suitable acids are sulfuric, phosphoric, hydrochloric, acetic, trichloroacetic or formic acids for example. The reaction can occur either in an aqueous medium or in an anhydrous organic medium. Aqueous formic acid is preferred. Inert organic solvents are ethers, e.g. dioxan or tetrahydrofuran, or a hydrocarbon or a mixture of hydrocarbons.

Though the temperature does not play a determining role, it could be observed that by effecting the reaction at a temperature in the vicinity of the boiling point of the reaction mixture, the yields were high and the reaction time was short. The thus obtained β-damascenone was finally isolated and purified according to the usual techniques, extraction with organic solvents and fractional distillation, for example. With respect to its organoleptic quality, this latter was found in complete accordance with the standards already existing in the perfume and flavor industry.

The organo-metallic derivative of formula (III) used as starting material in the invention process can be obtained according to the usual techniques by treating the corresponding acetylenic derivative with an alky-magnesium halide.

Oxophorone is a known compound which can be prepared on industrial scale following the process disclosed in U.S. Pat. No. 3,944,620.

The invention will be illustrated by the following examples (temperatures given in degrees centrigrade).

EXAMPLE 1

2,6,6-Trimethyl-1-hydroxy-1-(3-tert-butoxy-1-butyn-1-yl)-2-cyclohexen-4-one

Method A

A solution of 28.4 g (0.26M) of ethyl bromide in 500 ml of anhydrous ether was added dropwise to a suspension of 6.24 g (0.26 atom-gr) of magnesium turnings in 30 ml of anhydrous ether. After complete desappearance of magnesium, the mixture was cooled to room temperature and 32.8 g (0.26M) of butynyl-tert-butyl ether in 50 ml of ether were added thereto under stirring. After having been kept under stirring at room temperature overnight, the resulting ethyl-magnesium bromide was added under stirring to a solution of 30.4 g (0.2M) of oxophorone in 70 ml of anhydrous ether. The addition occurs in 45 min while the temperature increases from 25° to 35°, whereupon the mixture was kept under stirring overnight. After hydrolysis in a concentrated aqueous solution of ammonium chloride, the mixture was taken up with ether and the ethereal phase was washed, dried and concentrated to give 52 g of a residue that on bulb distillation at 13.3 Pa gave 48.9 g (yield 84%) of the described hydroxy ketone.

IR: 3450 and 1670 cm$^{-1}$;

NMR: 1.13 and 1.23 (6H, 2s); 1.25 (9H, s); 1.41 (3H, d,J≃6 Hz); 2.12 (3H, s); 2.47 (2H, s); 4.17 to 4.52 (1H, m); 5.84 (1H, s)δppm;

MS: M$^+$=278(≧0.1); m/e: 262(0.1), 222(3), 205(1), 191(11), 166(51), 148(100), 137(20), 124(27), 91(35), 77(28), 57(93), 41(76).

Method B

Ethyl magnesium bromide was prepared as described in method A above. The obtained mixture was cooled to 5°, then a solution of 30.4 g (0.2M) of oxophorone in 70 ml of ether has been added thereto within 20 min. The mixture was kept stirring for 15 h at room temperature after which one could notice the complete consumption of starting oxophorone. 47.3 G of the desired product (yield 72.3%) were thus obtained according to the procedure described under method A above.

Butynyl-tert-butyl ether, used as starting material in the above described process, is a commercially available material; it can be obtained from 3-butyn-2-ol and isobutylene.

EXAMPLE 2

2,6,6-Trimethyl-4-hydroxy-1(2-tert-butyloxy-3,4-butadien-4-yl)-2-cyclohexene

Method A (reduction with OMH)

The magnesium bromide derivative of 2,6,6-trimethyl-1-hydroxy-1-(3-tert-butoxy-1-butyne-1-yl)-2-cyclohexen-4-one was prepared as indicated under method A of example 1. The mixture was then reduced by adding dropwise thereto 200 ml (0.4M) of OMH at 25% in toluene (addition time: 1 h 30). The mixture was kept under stirring overnight, cooled with an external ice-water bath and hydrolysed by carefully adding thereto 300 ml of a 10% acetic acid solution, followed by 200 ml of 10% HCl. After dilution with ether, the organic phase was separated, washed with 2N NaOH and with water until neutrality, dried and concentrated. 44.5 G raw material were thus obtained.

An analytical sample of the desired product was prepared by purification via vapor phase chromatography.

IR: 3400, 1940 and 1070 cm$^{-1}$;

NMR: 1.1 and 1.17 (6H, 2s); 1.22 (9H, s); 1.23 (3H, d, J≃6 Hz); 1.8 (3H, s); 2.0 (2H, s); 4.1–4.55 (2H, m); 5.5–5.97 (2H, m)δppm;

MS: M$^+$=264(≧0.1); m/e: 246(1), 231(0,1), 210(0.1), 194(0.1), 175(3), 162(7), 147(8), 131(7), 109(1), 101(17), 84(35), 68(10), 59(39), 57(100), 41(35).

Method B (reduction with LiAlH$_4$)

13.3 G (0.35M) of sodium aluminum hydride were added portionwise to the mixture of magnesium bromide derivative prepared according to example 1, method A. After having been left overnight at room temperature, the mixture was cooled and hydrolysed with caution by adding water thereto followed by 10% HCl. After dilution with ether, the organic phase was separated, washed, dried and concentrated to give 41.1 g of raw material. This product was identical to that obtained in accordance with method A above.

The allenic carbinol obtained according to method B above (4.45 g) was heated to reflux in 250 ml of 50% formic acid and 250 ml of dioxan. The course of the reaction was followed by gas chromatographic control. After 2 h 30, the reaction mixture was cooled by means of an external ice bath, diluted with ether and the organic phase was washed with water, a 2N NaOH solution and again with water until neutrality. After drying and concentration, the obtained residue (4.23 g) of raw material gave by distillation 2.09 g of a product having a content of β-damascenone of about 68% (yield 35% calculated on starting oxophorone).

What we claim is:

1. An acetylenic carbinol of formula

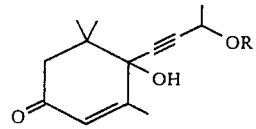

wherein symbol R stands for a trialkyl-silyl or a $C_1$ to $C_6$ alkyl radical, or a group of formula

wherein, when taken separately each of symbols $R^1$ and $R^2$ represents a lower alkyl radical, or when taken together, $R^1$ and $R^2$ represent a tetramethylene group.

2. The compound of claim 1 wherein R stands for a methyl, a tert-butyl or an isoamyl radical.

* * * * *